US012774365B2

(12) United States Patent
Yu et al.

(10) Patent No.: US 12,774,365 B2
(45) Date of Patent: Oct. 27, 2026

(54) POLYISOCYANATE COMPOSITION, PREPARATION METHOD THEREFOR AND APPLICATION THEREOF

(71) Applicants: WANHUA CHEMICAL GROUP CO., LTD, Yantai (CN); WANHUA CHEMICAL (NINGBO) CO., LTD, Ningbo (CN)

(72) Inventors: Yong Yu, Yantai (CN); Xuelei Cui, Yantai (CN); Yaoyun Guo, Yantai (CN); Yonghua Shang, Yantai (CN); Jinping Han, Yantai (CN); WenBin Li, Yantai (CN); Degang Liu, Yantai (CN); Yuan Li, Yantai (CN)

(73) Assignees: Wanhua Chemical Group Co., LTD, Yantai (CN); Wanhua Chemical (NINGBO) Co., LTD., Ningbo (CN)

( * ) Notice: Subject to any disclaimer, the term of this patent is extended or adjusted under 35 U.S.C. 154(b) by 616 days.

(21) Appl. No.: 18/253,868

(22) PCT Filed: Dec. 1, 2020

(86) PCT No.: PCT/CN2020/133079

§ 371 (c)(1),
(2) Date: May 22, 2023

(87) PCT Pub. No.: WO2022/115990

PCT Pub. Date: Jun. 9, 2022

(65) Prior Publication Data

US 2023/0374194 A1 Nov. 23, 2023

(51) Int. Cl.

| | |
|---|---|
| ***C07C 263/10*** | (2006.01) |
| ***C08G 18/10*** | (2006.01) |
| ***C08G 18/32*** | (2006.01) |
| ***C08G 18/48*** | (2006.01) |
| ***C08G 18/66*** | (2006.01) |
| ***C08G 18/73*** | (2006.01) |
| ***C08G 18/75*** | (2006.01) |

(52) U.S. Cl.

CPC ........ *C08G 18/6618* (2013.01); *C07C 263/10* (2013.01); *C08G 18/10* (2013.01); *C08G 18/3228* (2013.01); *C08G 18/48* (2013.01); *C08G 18/73* (2013.01); *C08G 18/758* (2013.01)

(58) Field of Classification Search

CPC .... C08G 18/82; C08G 18/755; C08G 18/758; C07C 263/10

See application file for complete search history.

(56) References Cited

U.S. PATENT DOCUMENTS

| | | | |
|---|---|---|---|
| 5,576,412 A | 11/1996 | Hirata et al. | |
| 2018/0162986 A1 | 6/2018 | Nakagawa et al. | |
| 2018/0171065 A1 | 6/2018 | Nakagawa et al. | |
| 2020/0190249 A1* | 6/2020 | Yamasaki | C08G 18/76 |

FOREIGN PATENT DOCUMENTS

| | | |
|---|---|---|
| CN | 1064074 | 9/1992 |
| CN | 1827593 | 9/2006 |
| CN | 1829685 | 9/2006 |
| CN | 102260194 | 11/2011 |
| CN | 103319372 | 9/2013 |
| CN | 105214568 | 1/2016 |
| CN | 105218422 | 1/2016 |
| CN | 107337615 | 11/2017 |
| CN | 109761855 | 5/2019 |
| CN | 110511163 | 11/2019 |
| CN | 110982038 | 4/2020 |
| CN | 111217975 | 6/2020 |
| EP | 2684867 A1 | 1/2014 |
| EP | 3901133 A1 | 10/2021 |
| JP | 53119823 A | 10/1978 |
| JP | 04145059 | 5/1992 |
| JP | 07278088 A | 10/1995 |
| JP | 0820625 | 1/1996 |

(Continued)

OTHER PUBLICATIONS

PCT Search Report and Written Opinion prepared for PCT Application No. PCT/CN2020/133079, completed Aug. 17, 2021.
Ying, Liu, et al., "SN2 Mechanism," 2017, Organic Chemistry (machine English translation).
Zhou Ling, et al., "The Influence of TDI Quality on Its Application," 2016, Polyurethane Industry, China Academic Journal Electronic Publishing House, vol. 31, No. 5, pp. 45-46 (English translation of abstract only).
Technical Data Sheet, Basf: "Lupranat MES", 2019, Retrieved from the Internet: URL:https://chemicals.basf.com/global/monomers/tds_isocyanate/lupranat/Lupranat%20MES.pdf, XP093155860.

(Continued)

*Primary Examiner* — Michael L Leonard
(74) *Attorney, Agent, or Firm* — EVAN LAW GROUP LLC

(57) ABSTRACT

A polyisocyanate composition, a preparation method therefor and an application thereof. The value of the mass content of alkaline hydrolyzed chlorine minus the mass content of water hydrolyzed chlorine in the polyisocyanate composition is 0.1 ppm-100 ppm. The mass content of the alkaline hydrolyzed chlorine is the mass content obtained by calculating halogen dissociated under alkaline conditions and/or halogen dissociated under a temperature condition of 100° C. or more as the relative atomic mass of a chlorine atom. In the polyisocyanate composition containing a specific amount of alkaline hydrolyzed chlorine, when a reaction locally becomes out of control causing causes a local severe exotherm, chlorine in alkaline hydrolyzed chlorine will be dissociated and be toxic to catalysts, thereby reducing the reactivity in local overreactive areas to thereby avoid the turbidity of a polyurethane synthetic emulsion, such that the light transmittance and yellowing resistance of polyurethane products are further improved.

17 Claims, No Drawings

(56) References Cited

FOREIGN PATENT DOCUMENTS

| | | | |
|---|---|---|---|
| JP | 09323968 | A | 12/1997 |
| JP | 2000044527 | | 2/2000 |
| JP | 2004027160 | | 1/2004 |
| JP | 2006232797 | A | 9/2006 |
| JP | 2015028163 | | 2/2015 |
| WO | 2020124622 | A1 | 6/2020 |

OTHER PUBLICATIONS

Technical Data Sheet, Basf: "Lupranat MEB", 2019, Retrieved from the Internet: URL:https://chemicals.basf.com/global/monomers/tds_isocyanate/lupranat/Lupranat%20MEB.pdf, XP093155870.

Technical Data Sheet, Basf: "Lupranat MRSA frozen", 2019, Retrieved from the Internet: URL:https://chemicals.basf.com/global/monomers/tds_isocyanate/lupranat/Lupranat%20MRSA%20frozen.pdf, XP093155857.

Technical Data Sheet, Basf: "Lupranat MR/MRS", 2019, Retrieved from the Internet: URL:https://chemicals.basf.com/global/monomers/tds_isocyanate/lupranat/Lupranat%20MR-MRS.pdf, XP093155864.

JIS K 1603-3, "Plastics—Test methods for aromatic isocyanates used as raw materials for polyurethanes—Part 3: Determination of hydrolyzable chlorine," 2007, URL: https://kikakurui.com/k1/K1603-3-2007-01.html (machine English translation).

European Search Report issued for Application No. 20963839, mailed May 17, 2024.

English Translation of Japanese Office Action issued for Application No. 2023-524847, mailed Mar. 7, 2024.

* cited by examiner

POLYISOCYANATE COMPOSITION, PREPARATION METHOD THEREFOR AND APPLICATION THEREOF

CROSS-REFERENCE TO RELATED APPLICATIONS:

This application is a national stage entry under 35 U.S.C. § 371 (b) of PCT International Application No. PCT/CN2020/133079, filed Dec. 1, 2020, the disclosure of of which is hereby incorporated by reference in its entirety.

TECHNICAL FIELD

The present application relates to the technical field of polyurethane, and in particular to a polyisocyanate composition and a preparation method therefor and use thereof.

BACKGROUND

Polyurethane is one of the synthetic resins with excellent overall performance. Due to its variety of synthetic monomers, mild reaction conditions, specifity, controllability, widely adjustable formulation, and the polymer material microstructural characteristics, the polyurethane can be widely used in coatings, adhesives, foams, synthetic fibers and elastomers, and has become one of the essential materials for clothing, food, housing and transportation; moreover, the polyurethane has formed a multi-species and multi-series material family by itself, and formed a complete Polyurethane industrial system, which is not available for other resins.

In the process of large-scale polyurethane production, due to the defects of the equipment or the poor mixing effect, the reaction concentration in the local region of the reaction space may be too high and the reaction may thus be overly violent, generating a large amount of heat to impel the reaction to proceed overly, causing the reaction to lose control locally, also leading to the turbidity of the polyurethane synthetic emulsion, which eventually leads to the failure of polyurethane products.

In the current industry standards, the impact of hydrolyzed chlorine impurities in polyisocyanate on the downstream polyurethane industry has been known. For example, in the national standard GB/T 37042-2018 for hexamethylene diisocyanate, it is clearly proposed to control the hydrolyzed chlorine within 100 ppm. For example, in patent CN103319372A, it is proposed to control the alcohol impurities in the raw material, and in patent CN109761855A, it is proposed to control the content of secondary amines in raw amines, the purpose of which is to reduce the content of hydrolyzed chlorine in the product.

CN110511163A discloses a method of preparing polyisocyanate by a phosgenation reaction and a method of preparing an aqueous polyurethane resin, specifically disclosing that the chlorine content in polyisocyanate can affect the yellowing resistance of the aqueous polyurethane resin, and may even directly cause yellowing of aqueous polyurethane resin, and may also adversely affect the reactivity of some systems.

CN1064074A discloses a method for reducing the content of hydrolyzable chloride in toluene diisocyanate, particularly its distillation residue. The application specifically discloses that if the content of hydrolyzable chloride in diisocyanate is too high, the diisocyanate will be unstable in viscidity and inactive, and therefore a treatment is required to reduce the hydrolyzable chloride content to a level where the residue is active and stable in viscidity.

Therefore, there is an urgent need in this field to establish a solution to further improve the quality of polyurethane products.

SUMMARY

The following is an overview of the subject described in detail herein. This overview is not intended to limit the protection scope of the claims.

A first object of the present application is to provide a polyisocyanate composition, and the polyisocyanate composition can solve the problem of unstable reactivity, which easily occurs in the pre-polymerization stage and chain expansion stage during the synthesis of polyurethane, and effectively relieve the turbidity of synthetic emulsions, thus improving the light transmittance and yellowing resistance of polyurethane products.

To achieve the object, the present application adopts the following technical solutions.

The present application provides a polyisocyanate composition, and a mass content of alkaline-dissociated chlorine minus a mass content of hydrolyzed chlorine has a value of 0.1 ppm-100 ppm, such as 0.2 ppm, 0.3 ppm, 0.4 ppm, 0.5 ppm, 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, ppm, 50 ppm, 55 ppm, 60 ppm, 65 ppm, 70 ppm, 75 ppm, 80 ppm, 85 ppm, 90 ppm, 95 ppm, 98 ppm, etc;

the mass content of the alkaline-dissociated chlorine is a mass content obtained by calculation based on halogen dissociated under alkaline condition and/or halogen dissociated at more than or equal to 100° C. with the relative atomic mass of chlorine atom.

The polyisocyanate composition in the present application includes impurities in addition to polyisocyanate and are therefore referred to as a composition, in which the polyisocyanate refers to isocyanate containing at least two (such as 2, 3, 4, etc.) isocyanate groups (O═C═N—). In the present application, the concept of hydrolyzed chlorine is common knowledge in the art.

The calculation with the relative atomic mass of chlorine atom in the present application means that: the detected amount or molar content of the dissociated halogen is converted into mass or mass content, regardless of the specific species, all based on the relative atomic mass of chlorine atom (35.45 g/mol). For example, in the case where the dissociated halogen is bromine and the amount of substance is 1 mol, the mass of alkaline-dissociated chlorine is 1 mol×35.45 g/mol=35.45 g, and the mass content of alkaline-dissociated chlorine is obtained from dividing the mass of alkaline-dissociated chlorine by the total mass of the polyisocyanate composition.

Due to the different formulations of the downstream polyurethane preparation process, the acidic and alkaline environment and reaction temperature conditions of the polyurethane synthesis process are also different, and chlorine can generally dissociate from an alkaline-dissociated chlorine impurity in the polyisocyanate composition during the polyurethane synthesis.

Based on the study of the inventor, a polyisocyanate composition containing a specific amount of alkaline-dissociated chlorine is provided. When the reaction loses control locally and thus intensely generates heat, the chlorine in alkaline-dissociated chlorine will dissociate and poison the catalyst, and thus reduce the reactivity of the local over-reaction region, thereby preventing the polyurethane synthetic emulsion from becoming turbid, and thus improving the light transmittance and yellowing resistance of polyurethane products.

However, when the amount of alkaline-dissociated chlorine is higher than a certain level, the chlorine dissociated under alkaline conditions will spread further outward after suppressing the local over-reaction, and poison the catalyst in the normal reaction region, leading to the unstable reaction activity and also the problematical thermal control of the synthesis process, which results in turbid polyurethane synthetic emulsion, adversely affects the polyurethane products, reduces light transmittance, and deteriorates the yellowing resistance.

Preferably, the mass content of alkaline-dissociated chlorine minus the mass content of hydrolyzed chlorine has a value of 0.2 ppm-60 ppm in the polyisocyanate composition, preferably 0.4 ppm-40 ppm.

In a preferred technical solution of the present application, the value of the mass content of alkaline-dissociated chlorine minus the mass content of hydrolyzed chlorine is further optimized, which thus can further relieve the turbidity problem of the polyurethane synthetic emulsion and improve the light transmittance and yellowing resistance of the product. If the amount of alkaline-dissociated chlorine is too low, the turbidity problem of polyurethane synthetic emulsion will be aggravated and the light transmittance of polyurethane products will be reduced, and if the amount of alkaline-dissociated chlorine is too high, not only the turbidity problem of synthetic emulsion will be aggravated and the light transmittance of polyurethane products will be reduced, but also the yellowing resistance will be deteriorated.

Preferably, the halogen includes any one or a combination of at least two of fluorine, chlorine, bromine or iodine.

Preferably, the polyisocyanate composition includes a combination of polyisocyanate, an alkaline-dissociated chlorine impurity and a hydrolyzed chlorine impurity. The alkaline-dissociated chlorine impurity is a substance that can be dissociated to obtain alkaline-dissociated chlorine, and the hydrolyzed chlorine impurity is a substance that can be dissociated to obtain hydrolyzed chlorine.

Based on the study of the inventor of the present application, it is found that one of the sources of alkaline-dissociated chlorine impurity is that: during the phosgenation reaction, the olefin structure, which is formed after the main product polyisocyanate loses one isocyanate group, further combined with hydrogen chloride in the phosgenation environment.

Different control methods are required for alkaline-dissociated chlorines from different sources. In the present application, the alkaline-dissociated chlorine in polyisocyanate is difficult to remove by conventional separation method, or requires large energy and material consumption to remove, which thus needs to be controlled at source.

Preferably, the polyisocyanate is diisocyanate.

Preferably, the polyisocyanate includes any one or a combination of at least two of alicyclic diisocyanate, aromatic diisocyanate or chain diisocyanate.

Preferably, the polyisocyanate includes any one or a combination of at least two of dicyclohexylmethane diisocyanate, isophorone diisocyanate, hexamethylene diisocyanate, m-xylylene diisocyanate, p-xylylene diisocyanate, 1,3-dimethyl isocyanate cyclohexane, 1,4-dimethyl isocyanate cyclohexane, tetramethylene diisocyanate, pentamethylene diisocyanate, toluene diisocyanate (TDI), diphenylmethane diisocyanate (MDI), benzene diisocyanate, naphthalene diisocyanate or cyclohexyl diisocyanate.

Preferably, the polyisocyanate includes dicyclohexylmethane diisocyanate, and the alkaline-dissociated chlorine impurity includes any one or a combination of at least two of the following compounds:

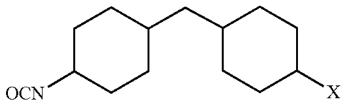

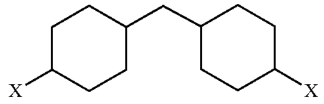

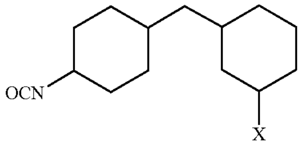

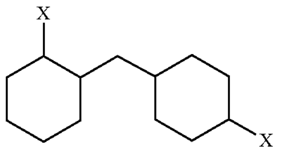

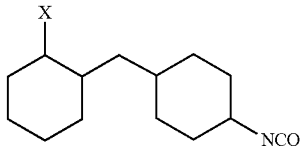

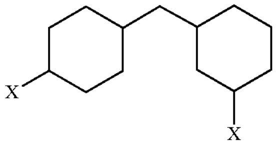
;

wherein X is F, Cl, Br or I.

Preferably, the polyisocyanate includes isophorone diisocyanate, and the alkaline-dissociated chlorine impurity includes any one or a combination of at least two of the following compounds:

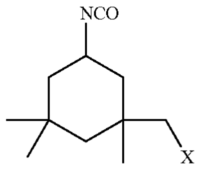
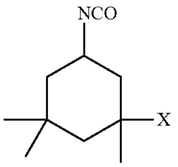
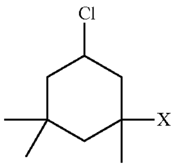

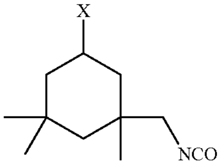
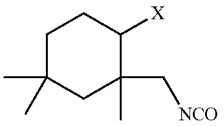

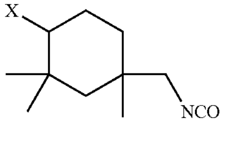
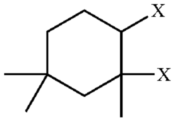

-continued

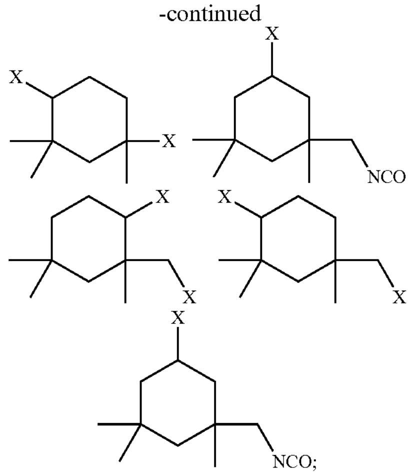

wherein X is F, Cl, Br or I.

Preferably, the polyisocyanate includes hexamethylene diisocyanate, and the alkaline-dissociated chlorine impurity includes any one or a combination of at least two of the following compounds:

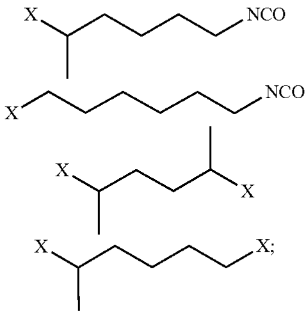

wherein X is F, Cl, Br or I.

Preferably, the polyisocyanate composition further includes an anti-aging additive. The anti-aging additive is added to enhance the storage stability of the polyisocyanate composition, extend its shelf life, and facilitate a stable color that is not easily turn to yellow during the preparation of polyurethane resin using the polyisocyanate composition in the present application.

Preferably, the anti-aging additive includes any one or a combination of at least two of a hindered phenolic antioxidant, a sulfonamide compound or organic phosphite ester, preferably a hindered phenolic antioxidant, further preferably any one or a combination of at least two of antioxidant 264 (for example, Eastman Chemical Company, Tenox BHT, USA), antioxidant 245 (for example, BASF, Irganox 245, Germany) or antioxidant 1076 (for example, BASF, Irganox 1076, Germany).

Preferably, a mass content of the anti-aging additive in the polyisocyanate composition is 50-5000 ppm, such as 100 ppm, 500 ppm, 1000 ppm, 1500 ppm, 2000 ppm, 2500 ppm, 3000 ppm, 3500 ppm, 4000 ppm, 4500 ppm, etc., preferably 100-1000 ppm.

Preferably, a raw material for preparing the polyisocyanate composition includes a combination of polyamine and a phosgene raw material. In the present application, the polyamine refer to a compound containing at least two (such as 2, 3, 4, etc.) amino groups.

Preferably, impurities having an olefin structure, a secondary amine structure or a hydroxyl structure in the polyamine have a total mass content of 0.1 ppm-400 ppm, such as 0.5 ppm, 1 ppm, 5 ppm, 10 ppm, 50 ppm, 100 ppm, 150 ppm, 200 ppm, 250 ppm, 300 ppm, 350 ppm, etc.

Based on the study of the inventor of the present application, another source of the alkaline-dissociated chlorine is that: some components introduced during the preparation of the polyamine raw material produce alkaline-dissociated chlorines in the subsequent phosgenation process when preparing isocyanate, and the specific structure includes, but is not limited to, the following: a) an olefin structure, b) a secondary amine structure, and c) a hydroxyl structure.

Substances containing the above structures are generally difficult to separate from the raw material polyamine, and can react with phosgene or hydrogen chloride during the phosgenation process, especially the gas-phase phosgenation process, thus forming alkaline-dissociated chlorines. Therefore, the total amount of these kinds of substances needs to be controlled in terms of the polyamine raw material. In the present application, it is proposed to control the total amount at 0.1 ppm-400 ppm.

In the present application, the determination of the mass content of the hydrolyzed chlorine is known in the prior art, including but not limited to the method provided in GB/T 37042-2018. As for the mass content of the alkaline-dissociated chlorine, those skilled in the art can also use the conventional methods. The present application only provides the following determination method exemplarily, but the determination is not limited to the following method.

The determination principle of this method includes: the alkali-dissociable chlorine in polyisocyanate is mainly the chlorine that can be dissociated down under alkaline conditions; firstly, the isocyanate in polyisocyanate will be removed through the reaction between ethanol and polyisocyanate, and then the alkali-dissociable halogen will be dissociated down under alkaline conditions, and the dissociated halogen ions will form the corresponding salt, and then determined for the content with silver nitrate standard solution by potentiometric titration.

Instruments used in the determination procedure are as follows:

(a) potentiometric titrator;

(b) composite silver electrode;

(c) electromagnetic stirrer;

(d) constant-temperature water bath: 80° C.;

(e) general experimental apparatus.

Reagents used for the determination procedure are as follows:

(a) water: water treated by ion exchange resin;

(b) acetone (AR);

(c) nitric acid solution: nitric acid (GB626) and water mixed by 1:3 in volume;

(d) sodium chloride standard solution: 1 mL is equivalent to 1 mg, prepared by the method specified in GB601;

(e) silver nitrate standard solution: $C(AgNO_3)$=0.05 mol/L, prepared and calibrated using the method specified in GB601;

(f) ethanol (AR);

(g) sodium hydroxide standard solution (2 mol/L): 80 g of sodium hydroxide (GB629) is weighed and dissolved with water and diluted to 1000 mL.

Exemplarily, the specific determination steps are as follows:

(a) 10 g-15 g (accurate to 0.1 mg) of the sample is weighed out and added in a 300 mL beaker, a rotor and 30 mL of acetone are added, and when the sample is completely dissolved, 50 mL of ethanol solution is added, and the system is placed into a constant-temperature water bath at 60° C. for a sufficient reaction;

(b) after 30 min of the reaction, 100 mL of NaOH solution is added and the reaction is continued in the constant-temperature water bath at 60° C. for 50 min;

(c) the beaker is taken out and transferred to an ice water bath to cool down to less than or equal to 10° C.;

(d) 2 mL of sodium chloride standard solution is accurately added in a beaker, and then added with 20 mL of 1:3 nitric acid solution; the potentiometric titration is performed, the inflection point of the resulting curve is selected as the end point, and the volume of silver nitrate standard solution consumed is recorded;

(e) a blank test is performed at the same time.

The alkaline-dissociated chlorine is calculated by the following equation:

$$Cl = \frac{(V - V_0) \times C \times 0.03546}{m} \times 10^6;$$

in the formula: Cl—percentage of hydrolyzed chlorine (in chlorine), ppm;

V—volume of silver nitrate standard solution consumed in the titration of sample, mL;

$V_0$—volume of silver nitrate standard solution consumed in the titration of blank, mL;

C—actual concentration of silver nitrate standard solution, mol/L;

m—mass of sample, g;

0.03546—equivalent to 1.00 mL of silver nitrate standard solution [$C(AgNO_3)$=1.000 mol/L], the mass of chlorine atom expressed in grams, in g/mol.

A second object of the present application is to provide a preparation method of the polyisocyanate composition according to the first object, and the preparation method includes: subjecting polyamine and a phosgene raw material to a phosgenation reaction to obtain the polyisocyanate composition.

Preferably, the polyamine includes any one or a combination of at least two of m-phenylenedimethylamine, p-phenylenedimethylamine, 1,3-cyclohexanedimethanamine, 1,4-cyclohexanedimethanamine, 1,4-butanediamine, 1,6-hexanediamine, 1,4-diaminocyclohexane, diaminodicyclohexylmethane (for example, industrial product $H_{12}$MDA, which is a mixture containing 4,4-diaminodicyclohexylmethane, 2,4-diaminodicyclohexylmethane, 2,2-diaminodicyclohexylmethane, etc.), toluenediamine, methylene diphenylamine (for example, 2,2'-methylenedianiline, 4,4'-methylenedianiline), isophorone diamine, phenylenediamine, naphthalene diamine, 1,8-octanediamine, 1,10-decanediamine, 1,12-diaminododecane, 1,5-pentanediamine, cyclohexanediamine, methylcyclohexanediamine, tetramethyl-p-phenylenediamine, or dimethyl-biphenylenediamine Preferably, the polyamine includes any one or a combination of at least two of m-phenylenedimethylamine, p-phenylenedimethylamine, 1,3-cyclohexanedimethanamine, 1,4-cyclohexanedimethanamine, 1,4-butanediamine, 1,6-hexanediamine, 1,4-diaminocyclohexane, diaminodicyclohexylmethane (for example, industrial product $H_{12}$MDA, which is a mixture containing 4,4-diaminodicyclohexylmethane, 2,4-diaminodicyclohexylmethane, 2,2-diaminodicyclohexylmethane, etc.), isophorone diamine, 1,8-octanediamine, 1,10-decanediamine, 1,12-diaminododecane, 1,5-pentanediamine, cyclohexanediamine, methylcyclohexanediamine, tetramethyl-p-phenylenediamine, dimethyl-biphenylenediamine, 1,6-hexanediamine, diaminodicyclohexylmethane, toluenediamine, phenylenediamine, or naphthalene diamine.

Preferably, the phosgene raw material is fed excessively.

Preferably, the phosgene raw material includes any one or a combination of at least two of phosgene, diphosgene, triphosgene, fluorophosgene or bromophosgene, preferably any one or a combination of at least two of phosgene, diphosgene, triphosgene or fluorophosgene, and more preferably phosgene and/or fluorophosgene.

Preferably, the preparation method further includes subjecting the crude product obtained from the phosgenation reaction to post-treatment.

Preferably, the phosgenation reaction includes a gas-phase phosgenation reaction, a liquid-phase phosgenation reaction or a salt-forming phosgenation reaction.

The phosgenation reaction of the present application can be performed using technical process known in the art. According to the method provided in the present application, in some examples, the phosgenation reaction is selected from a gas-phase phosgenation reaction, a liquid-phase phosgenation reaction or a salt-forming phosgenation reaction. In different phosgenation reaction processes, different methods are required to control the alkaline-dissociated chlorine content.

Preferably, the gas-phase phosgenation reaction includes: subjecting a polyamine gas stream and the phosgene raw material to a gas-phase phosgenation reaction, and mixing a reaction product with a liquid inert medium and cooling to less than or equal to 150° C., or, mixing a reaction product with a liquid inert medium and a target isocyanate product mixture and cooling to less than or equal to 150° C., such as 50° C., 60° C., 70° C., 80° C., 90° C., 100° C., 110° C. 120° C., 130° C., 140° C., 150° C., etc., and preferably 100-140° C., to obtain a crude isocyanate product.

In a preferred technical solution of the present application, due to the high temperature of the reaction gas mixture and in order to control the generation of alkaline-dissociated chlorine, the temperature of the reaction gas mixture is required to be less than or equal to 150° C. after being absorbed and cooled by the liquid inert medium and/or the mixture of inert medium and isocyanate to reduce the generation of alkaline-dissociated chlorine.

Exemplarily, the gas-phase phosgenation reaction can be found in applications CN102260194A and CN105214568A. In some embodiments, steps of the gas-phase phosgenation reaction include: 1) polyamine is gasified to form a polyamine gas stream containing polyamine droplets; 2) the polyamine droplets contained in the polyamine gas stream are removed to obtain a polyamine gas stream substantially free of polyamine droplets; and 3) the polyamine gas stream substantially free of polyamine droplets and a phosgene raw material are subjected to the gas-phase phosgenation reaction, the reaction product is mixed with a liquid inert medium (such as an aromatic solvent) and rapidly cooled to 100-140° C. vis a gas jet absorption device, or, the reaction product is mixed with a mixture of a liquid inert medium and a target isocyanate product and rapidly cooled to 100-140° C. via a gas jet absorption device to obtain the crude isocyanate product. At the same time, the polyamine droplets contained in the polyamine gas stream are removed by a heater; for example, the specific structure of the heater used can be found in application CN105214568A. The gas-phase phosgenation reaction is performed at, for example, 200-550° C. (such as 250° C., 300° C., 320° C., 380° C., 420° C., 500° C.), preferably 250-400° C.; the reaction is performed at 0.01-1 MPa (such as 0.05 MPa, 0.08 MPa, 0.2 MPa, 0.5 MPa, 0.8 MPa), preferably 0.03-0.3 MPa. In some specific embodiments, the gas mixture (reaction product) obtained after the reaction of the phosgene raw material with the polyamine can be absorbed and cooled by a liquid inert medium (such as an aromatic solvent) and/or a mixture of an inert medium and isocyanate.

Preferably, the liquid-phase phosgenation reaction includes: subjecting a polyamine solution and the phosgene raw material to a cold reaction at 0-100° C. first and then to a hot reaction at 60-180° C., wherein the cold reaction and the hot reaction have a total retention time of less than or equal to 7h, such as 1 h, 2 h, 3 h, 4 h, 5h, 6h, 7h, etc.

In a preferred technical solution of the present application, the total retention time of the cold and hot reactions is controlled within 7 h to control the generation of alkaline-dissociated chlorine.

Exemplarily, the liquid-phase phosgenation reaction can be found in application CN103319372A. In some embodiments, the liquid-phase phosgenation reaction is performed in two steps: 1) cold reaction, a temperature is 0-100° C., preferably 40-70° C.; a pressure is 0.1-1 MPa (absolute pressure); the polyamine is mixed with an aromatic solvent (optionally selected from one or more of chlorobenzene, m-dichlorobenzene, o-dichlorobenzene, p-dichlorobenzene and chlorotoluene) and prepared into a solution to react with the phosgene raw material in an amount of more than stoichiometric dose; a reaction retention time can be 2-120 min, preferably 5-45 min; and 2) hot reaction, a temperature is 60-180° C., preferably 110-165° C., and more preferably 120-150° C.; a pressure is 0.1-1 MPa (absolute pressure); with one or more of chlorobenzene, m-dichlorobenzene, o-dichlorobenzene, p-dichlorobenzene and chlorotoluene as a solvent, the phosgene raw material in an amount of more than stoichiometric dose is reacted, a reaction retention time can be 0.5-5 h. In the liquid-phase phosgenation process, the cold reaction and the hot reaction have a total retention time of less than or equal to 7 h to control the generation of alkaline-dissociated chlorine.

Preferably, the salt-forming phosgenation reaction includes: subjecting the polyamine, hydrogen chloride and/or carbon dioxide to a salt-forming reaction in an inert solvent, and then subjecting the system and the phosgene raw material to a phosgenation reaction; the salt-forming reaction and the phosgenation reaction have a total retention time of less than or equal to 7 h, such as 1 h, 2 h, 3 h, 4 h, 5 h, 6 h, 7 h, etc.

In a preferred technical solution of the present application, the salt-forming reaction and the phosgenation reaction have a total retention time of less than or equal to 7 h to control the generation of alkaline-dissociated chlorine.

Exemplarily, the phosgenation reaction can also be performed in hydrogen chloride and/or carbon dioxide, i.e., the salt-forming phosgenation reaction, which can be found in application CN105218422A and CN107337615A. In some embodiments, steps of the salt-forming phosgenation reaction include: 1) polyamine, hydrogen chloride and/or carbon dioxide are subjected to a salt-forming reaction in an inert solvent; the hydrogen chloride and amino groups of the polyamine have a molar ratio of 1-2.5:1, preferably 1.2-2:1; the carbon dioxide and amino groups of the polyamine have a molar ratio of 0.5-5:1, preferably 0.6-3:1; the inert solvent and the polyamine have a mass ratio of 25-5:1, preferably 20-5:1; the salt-forming reaction is performed at 0-50° C., preferably 5-30° C., and at 0.1-1 MPa (absolute pressure), preferably 0.2-0.5 MPa (absolute pressure); a reaction retention time is 1-15 min, preferably 5-10 min; after the salt-forming reaction in step 1), the obtained reaction liquid of hydrochloride or carbonate is subjected to step 2) to react with the phosgene raw material for the phosgenation reaction; a reaction temperature is 100-170° C., preferably 110-165° C., and more preferably 120-150° C.; a reaction pressure is 0.1-1 MPa (absolute pressure), preferably 0.2-0.5 MPa (absolute pressure); the phosgene raw material in an amount of more than stoichiometric dose is reacted, a reaction retention time can be 1-8 h. In the reaction, the inert solvent is selected from one or more of chlorobenzene, m-dichlorobenzene, o-dichlorobenzene, p-dichlorobenzene and chlorotoluene. In the salt-forming phosgenation process, step 1) and step 2) have a total retention time of less than or equal to 7 h to control the generation of alkaline-dissociated chlorine.

When the reaction is completed, regardless of whether a liquid-phase, salt-forming or gas-phase phosgenation process is used, the reaction liquid can be filtered and subsequently separated as needed. According to the technology known in the art, the by-products of hydrogen chloride and excess phosgene raw material in the reaction liquid are usually removed using a distillation column or a stripping tower. The phosgene raw material can be conveyed back to the reaction system for recycling after refinement; the solvent in the reaction liquid is removed using a distillation column, and the solvent can be conveyed back to the reaction system for recycling after refinement; the crude polyisocyanate composition stream that substantially contains no solvent is obtained by separation. The crude polyisocyanate composition stream is separated and refined using a scraper evaporator or a distillation column, and the non-volatile components (tar) and low-boiling light component impurities are removed to obtain the polyisocyanate combination.

A third object of the present application is to provide a polyurethane resin, and a raw material to prepare the polyurethane resin includes a combination of the polyisocyanate composition according to the first object and a compound containing a reactive hydrogen group.

The polyurethane resin in the present application is a reaction product of the polyisocyanate component in the polyisocyanate composition and the compound containing a reactive hydrogen group. The polyurethane resin provided in the present application has low turbidity of the emulsion obtained in the synthesis process, light transmittance of the polyurethane products is high, and the yellowing resistance and heat resistance are good.

Preferably, the compound containing a reactive hydrogen group includes a polyol compound and/or an amine compound. The polyol compound is a compound having at least two hydroxyl groups.

Preferably, the polyol compound has a molecular mass of 400-20000, such as 800, 1000, 2000, 5000, 8000, 10000, 15000, 18000, etc.

Preferably, the polyol compound has a hydroxyl value of 10 mg KOH/g-1500 mg KOH/g, such as 20 mg KOH/g, 30 mg KOH/g, 40 mg KOH/g, 50 mg KOH/g, 100 mg KOH/g, 200 mg KOH/g, 500 mg KOH/g, 800 mg KOH/g, 1000 mg KOH/g, 1200 mg KOH/g, 1400 mg KOH/g, etc. The hydroxyl value of the polyol component can be analyzed and determined with reference to the A-phthalic anhydride method in GB/T 12008.3-2019 standard.

Preferably, the polyol compound has a functionality of 2-8, such as 3, 4, 5, 6, 7, etc.

Preferably, the polyol compound includes any one or a combination of at least two of polyether polyol, polyester polyol, polyolefin polyol, epoxy resin or bio-based polyol.

Preferably, the polyether polyol includes any one or a combination of at least two of polyethylene oxide polyol, poly(propylene oxide) polyol, polymer polyol, polyurea polyol, polytetrahydrofuran and its copolyether diol, polytrimethylene diol or aromatic polyether polyol.

Preferably, the polyester polyol includes any one or a combination of at least two of adipic acid polyester diol, an aromatic polyester polyol, a polycaprolactone polyol or a polycarbonate diol.

Preferably, the adipic acid polyester glycol includes any one or a combination of at least two of poly(ethylene adipate) diol, poly(propylene adipate) diol, poly(butylene adipate) diol or poly (diethylene glycol adipate).

Preferably, the aromatic polyester polyol includes any one or a combination of at least two of poly(diethylene glycol phthalate) diol, poly(1,6-hexanediol phthalate) diol or poly (neopentyl glycol phthalate) diol.

Preferably, the polycaprolactone polyol includes polycaprolactone diol and/or polycaprolactone triol.

Preferably, the polycarbonate diol includes any one or a combination of at least two of poly(hexylene carbonate) diol, poly(1,6-hexylene carbonate) diol or poly(butylene carbonate) diol.

Preferably, the polyolefin polyol includes any one or a combination of at least two of hydroxyl-terminated polybutadiene, hydroxyl-terminated hydrogenated polybutadiene, a hydroxyl-terminated epoxidized polybutadiene resin, hydroxyl-terminated polybutadiene-acrylonitrile or polystyrene polyol.

Preferably, the epoxy resin includes any one or a combination of at least two of a bisphenol A epoxy resin, a bisphenol F epoxy resin, a phenolic epoxy resin or an aliphatic epoxy resin.

Preferably, the bio-based polyol includes any one or a combination of at least two of castor oil and its derivative polyol, soybean oil polyol, palm oil polyol, rosin ester polyol, fatty acid dimer diol, fish oil polyol, or lignin polyol.

Preferably, the raw material to prepare the polyurethane resin further includes a catalyst and/or a chain extender.

Preferably, the chain extender includes any one or a combination of at least two of a polyfunctional alcohol compound (for example, having a functionality of 2, 3, 4, 5) and/or a polyfunctional amine compound (for example, having a functionality of 2, 3, 4, 5), preferably ethylene glycol, diethylene glycol, 1,2-propanediol, dipropylene glycol, 1,4-butanediol (BDO), 1,6-hexanediol (HD), trimethylolpropane (TMP), castor oil, ethylenediamine (EDA), hydrazine, hexanediamine, isophorone diamine, methyl pentanediamine, diethylenetriamine, or triethylene tetramine.

In the field of aqueous polyurethane, the chain extender used is any one or a combination of at least two of a hydrophilic chain extender, preferably dihydroxymethylpropionic acid (DMPA), dihydroxymethylbutyric acid (DMBA), sodium 1,4-butanediol-2-sulfonate, diethanolamine, triethanolamine, N-methyldiethanolamine (MDEA), N-ethyl diethanolamine (EDEA), N-propyl diethanolamine (PDEA), N-butyl diethanolamine (BDEA), dimethylethanolamine, bis(2-hydroxyethyl)aniline (BHBA), bis(2-hydroxypropyl)aniline (BHPA), and N-methyldiethanolamine (MDEA).

In the present application, the polyurethane resin can be prepared by a process route known in the art, such as one-step method and prepolymer method, and the prepolymer method is preferably used in the present application.

Exemplarily, the one-step method is a preparation method in which the required raw materials such as polyisocyanate (such as alicyclic diisocyanate composition), polyol, a catalyst, a chain extender, etc., are uniformly mixed in one step and cast molding.

Exemplarily, the prepolymer method is a preparation method in which polyol and a slight excess amount of polyisocyanate (such as an alicyclic diisocyanate composition) are reacted and produce polyurethane prepolymer with isocyanate capped ends, and then the prepolymer, a catalyst, and a chain extender are further reacted and cured and cast molding to obtain a polyurethane elastomer material.

In a specific embodiment of the present application, the polyurethane resin is prepared by the prepolymer method, which includes the following steps:

1) the polyol and an excess amount of the polyisocyanate composition are subjected to a pre-polymerization reaction to prepare polyurethane prepolymer with isocyanate capped ends; preferably, the pre-polymerization reaction is performed at 60-120° C., preferably 80-100° C., and for 1-6 h, preferably 2-4 h;
2) the polyurethane prepolymer is mixed with a catalyst and a chain extender and subjected to cast curing to obtain the polyurethane resin; preferably, the cast curing is performed at 50-100° C., preferably 60-80° C., and a temperature of the cast curing is 1-10 h, preferably 3-6 h.

In some embodiments, the raw material formulation used in the prepolymer method in the present application includes, by parts by mass, the following raw materials: 50-500 parts, preferably 100-400 parts, of the polyisocyanate composition; 100 parts of the polyol; 50-500 parts, preferably 50-400 parts, of the chain extender; and 0.005-1 part, preferably 0.01-0.5 parts, of the catalyst.

The chain extender may be a conventional chain extender in the art. For example, in some embodiments, the chain extender in the present application can be a bifunctional compound or a trifunctional compound or a compound with more functional groups. The bifunctional compound includes, for example, diols such as 1,4-butanediol, ethylene glycol, diethylene glycol, 1,6-hexanediol, etc., diamines such as 3,3'-dichloro-4,4'-diphenylmethanediamine (MOCA), 3,5-diethyltoluenediamine (DETDA), etc., and ethanolamine. The trifunctional compound and the compound with more functional groups include, for example, glycerol, trimethylolpropane, and pentaerythritol. The 1,4-butanediol and/or 3,3'-dichloro-4,4'-diphenylmethanediamine are preferred in the present application.

During the preparation of polyurethane resin in the present application, the content of isocyanate groups in the prepared isocyanate prepolymer can be titrated and analyzed using the method specified in the GB/T 12009.4-1989 standard.

The amount of chain extender can be calculated with reference to the method provided in application CN110982038A; the chain extender in the present application preferably has a chain extension coefficient of 0.8-1.1, more preferably 0.9-1.0.

The catalyst for the prepolymer method is generally an organotin compound, which includes, for example, one or more of stannous octanoate, dibutyltin dichloride, dibutyltin dilaurate, dibutyltin diacetate, and dibutyltin bis(dodecylthio), and dibutyltin dilaurate is preferred for the process route of the present application.

It should be noted that in the preparation of the polyurethane resin of the present application, additives known in the industry, such as plasticizers, defoamers, flame retardants, dehydrating agents, antioxidants, ultraviolet absorbers, anti-hydrolysis agents, weather resistant stabilizers, etc., can be further added in appropriate proportions according to the needs of specific applications.

A fourth object of the present application is to provide use of the polyurethane resin according to the third object, and the polyurethane resin is used in preparing polyurethane elastomers, polyurethane optical materials, polyurethane coating materials (such as coatings, adhesives) or polyurethane foams, preferably in preparing polyurethane elastomers Compared with the prior art, the present application has the following beneficial effects.

The present application provides a polyisocyanate composition containing a specific amount of alkaline-dissociated chlorine. When the reaction loses control locally and thus intensely generates heat, the chlorine in alkaline-dissociated chlorine will dissociate and poison the catalyst, and thus reduce the reactivity of the local over-reaction region, thereby preventing the polyurethane synthetic emulsion from becoming turbid, and thus improving the light transmittance and yellowing resistance of polyurethane products.

Other aspects can be understood after reading and understanding the detailed description.

DETAILED DESCRIPTION

The technical solutions of the present application are further described below through embodiments. It should be apparent to those skilled in the art that the embodiments are only used for a better understanding of the present application and should not be construed as a specific limitation of the present application.

Example 1

This example provides a polyisocyanate composition, and its preparation method is as follows.

a) Hexanediamine (HDA) was gasified and heated to 355° C. using the heater disclosed in Example 1 of application CN105214568A, and under the protection of nitrogen, and HAD and gaseous phosgene that was heated to 355° C. were continuously added to a reactor via their respective feed pipes for a phosgenation reaction; the reaction was performed at 0.05 MPa (absolute pressure) and at 360° C.; HDA was fed at 800 Kg/h and gaseous phosgene was fed at 3000 Kg/h; the gas mixture obtained from the reaction was cooled rapidly (with a contact time of about 10 s) to 100° C. using an o-dichlorobenzene solution via a gas injection absorption device to obtain a crude product containing HDI, phosgene and the o-dichlorobenzene solution;

the reaction tail gas was fed in a tail gas absorption tower and then absorbed with an o-dichlorobenzene solution at −35° C. to obtain an o-dichlorobenzene solution containing phosgene.

b) The crude product obtained from step a) was subjected to a treatment of removing phosgene and the o-dichlorobenzene solution, and the o-dichlorobenzene solution and excess phosgene in the crude product were removed at 168° C. and 0.1 MPa (absolute pressure) to obtain an HDI crude product without phosgene and an o-dichlorobenzene solution containing phosgene.

c) The o-dichlorobenzene solution containing phosgene obtained from the reaction tail gas absorption in step a) and the o-dichlorobenzene solution containing phosgene obtained from the removal process in step b) were fed in a distillation column for a separation of phosgene and o-dichlorobenzene solution; the separation process was performed at 0.125 MPa (absolute pressure), a column-bottom temperature of 155° C. and a column-top temperature of 15° C. to obtain phosgene with 98% purity and an o-dichlorobenzene solution with a phosgene content of less than 0.001%, and the separated phosgene and the o-dichlorobenzene solution were all subjected back to step a) for recycling.

d) The HDI crude product without phosgene obtained from step b) was purified by distillation at 0.5 KPa (absolute pressure) and a distillation range of 135-140° C. to obtain an HDI (hexamethylene diisocyanate) product.

An olefin structure, a secondary amine structure and a hydroxyl structure in the hexanediamine used had a total content of 200 ppm.

The yield of the HDI product obtained is 97% and the product purity is 99.75%. The product obtained contains 25 ppm of hydrolyzed chlorine and 30 ppm of alkaline-dissociated chlorine, and a difference between the alkaline-dissociated chlorine and the hydrolyzed chlorine is 5 ppm.

This example also provides a polyurethane resin, and its preparation method is as follows.

(1) Preparation of Polyurethane Prepolymer 100 parts of polyoxypropylene glycol were weighed out, which had a relative molecular mass of 1000, a hydroxyl value of 110 mg KOH/g, a functionality of 2 (Shanghai Gaoqiao Petrochemical Company, polyether polyol GE-210), heated to 110° C. with stirring, subjected to pressure reduction to 200 Pa (absolute pressure) to remove water for 2.5 hours, and cooled to 60° C., and 168 parts of the HDI produced during the above synthesis of the isocyanate were added. The system was heated to 80° C. and reacted for 120 min to obtain a blue transparent polyurethane prepolymer emulsion.

The turbidity test result for the prepolymer emulsion is 0.42 NTU.

(2) The polyurethane prepolymer obtained from step (1), 82 parts of 1,4-butanediol (BASF Corporation, after a water removal treatment at 102° C. and 200 Pa (absolute pressure) for 2.5 hours) and 0.1 part of dibutyltin dilaurate (Dabco T-12, Air Chemicals, USA) were added in a casting machine, heated to 45° C., respectively, subjected to pressure reduction to 1 Kpa (absolute pressure) and de-bubbled for 0.5 hours, mixed evenly, poured into a mold which had been preheated to 75° C., heated and cured for 4 h to obtain the polyurethane resin.

The obtained polyurethane product was tested for light transmittance according to the method provided by GB/T 2410-2008, and the result is 97.5%.

The obtained polyurethane resin was put into an oven at 80° C. and baked for 12 h to obtain a dried polyurethane product. The color value b of the polyurethane product was tested with a colorimeter (X-Rite 528), and then the polyurethane film was baked in an oven at 150° C. for 0.5 h. The color value b of the resin film after baking was tested with a colorimeter and the color difference ΔE was 0.45 (the lower the value, the better the performance), which showed that the polyurethane resin provided in this example has good yellowing resistance.

Example 2

This example provides a polyisocyanate composition, and its preparation method is as follows.

The phosgenation reaction in step a) is a liquid-phase phosgenation reaction, which is performed by the following steps in a tank reactor with reference to the disclosed application CN103319372A.

1) Cold reaction: 4,4'-diaminodicyclohexylmethane ($H_{12}MDA$) was prepared into a solution of 15% mass content with o-dichlorobenzene as the solvent and preheated to 40° C., and the prepared solution and liquid phosgene at −5° C. were simultaneously introduced into a tank reactor containing an o-dichlorobenzene solution for a liquid-phase phosgenation reaction; $H_{12}MDA$ was fed at 400 Kg/h, the phosgene for the cold reaction was fed at 1500 Kg/h, and a temperature of the cold reaction was controlled at 60° C. and a retention time was 5 min.
2) Hot reaction: a temperature of the hot reaction was controlled at 155° C. and a retention time was 6 h, and the hot reaction was performed in the presence of an o-dichlorobenzene solution and excess phosgene to obtain a reaction liquid (crude product) containing the product $H_{12}MDI$, phosgene and the o-dichlorobenzene solution.

The cold and hot phosgenation reaction stages had a total retention time of six hours and five minutes.

The reaction tail gas was fed in a tail gas absorption tower and then absorbed with an o-dichlorobenzene solution at −35° C. to obtain an o-dichlorobenzene solution containing phosgene.

b) The reaction liquid obtained from step a) was subjected to a treatment of removing phosgene and the o-dichlorobenzene solution, and the o-dichlorobenzene solution and excess phosgene in the reaction liquid were removed at 155° C. and 0.05 MPa (absolute pressure) to obtain an $H_{12}MDI$ crude product without phosgene and an o-dichlorobenzene solution containing phosgene.

During the removal process, the o-dichlorobenzene solution containing phosgene was controlled at 155° C. for a retention time of 1 h.

c) The o-dichlorobenzene solution containing phosgene obtained from the reaction tail gas absorption in step a) and the o-dichlorobenzene solution containing phosgene obtained from the removal process in step b) were fed in a distillation column for a separation of phosgene and o-dichlorobenzene; the separation process was performed at 0.125 MPa (absolute pressure), a column-bottom temperature of 145° C. and a column-top temperature of 15° C. to obtain phosgene with 98% purity and an o-dichlorobenzene solution with a phosgene content of less than 0.001%, and the separated phosgene and the o-dichlorobenzene solution were all subjected back to step a) for recycling.

d) The $H_{12}MDI$ crude product without phosgene obtained from step b) was purified by distillation at 0.5 KPa (absolute pressure) and a distillation range of 150-160° C. to obtain an $H_{12}MDI$ (dicyclohexylmethane diisocyanate) product.

An olefin structure, a secondary amine structure and a hydroxyl structure in the $H_{12}MDA$ used had a total content of 270 ppm.

The yield of the $H_{12}MDI$ product obtained is 96% and the product purity is 99.8%. The product obtained contains 5 ppm of hydrolyzed chlorine and 7 ppm of alkaline-dissociated chlorine, and a difference between the alkaline-dissociated chlorine and the hydrolyzed chlorine is 2 ppm.

This example also provides a polyurethane resin, and its preparation method is as follows.

(1) Preparation of Polyurethane Prepolymer 100 parts of polyoxypropylene glycol were weighed out, which had a relative molecular mass of 1000, a hydroxyl value of 110 mg KOH/g, a functionality of 2 (Shanghai Gaoqiao Petrochemical Company, polyether polyol GE-210), heated to 110° C. with stirring, subjected to pressure reduction to 200 Pa (absolute pressure) to remove water for 2.5 hours, and cooled to 60° C., and 262 parts of the $H_{12}MDI$ produced during the above synthesis of the isocyanate were added. The system was heated to 85° C. and reacted for 100 min to obtain a blue transparent polyurethane prepolymer emulsion.

The turbidity test result for the prepolymer emulsion is 0.25 NTU.

(2) The polyurethane prepolymer obtained from step (1) was prepared into the polyurethane resin and tested for color difference LE according to Example 1, and the result is 0.31. It is shown by the data that the polyurethane resin provided by this example has good yellowing resistance.

The obtained polyurethane product was tested for light transmittance according to the method provided by GB/T 2410-2008, and the result is 95.5%.

Example 3

This example provides a polyisocyanate composition, and its preparation method is as follows.

The phosgenation reaction in step a) is a salt-forming phosgenation reaction, which is performed by the following steps in a tank reactor with reference to the disclosed Example 1 in application CN05218422A.

1) 1000 Kg of o-dichlorobenzene was added in a salt-forming tank reactor as a reaction solvent in advance, a circulation pump and agitation were operated, compressed hydrogen chloride gas was introduced in the reactor at 50 mol/min via a premixer, and stirred for 15 min, and a mixed liquid of isophorone diamine (IPDA) and o-dichlorobenzene was heated to 30° C. through a raw material preheater, and fully contacted with hydrogen chloride gas at a flow rate of 335 Kg/h to generate a salt; the system was cooled by external circulating cooling water to remove part of the reaction heat, in which the circulating liquid had a flow rate of about 5 $m^3/h$, and the reaction liquid was maintained at 30-45° C., and after feeding for 1 h, the feeding of the mixed liquid of IPDA and o-dichlorobenzene was stopped, and HCl gas was continuously introduced for 30 min.
2) The IPDA hydrochloride slurry obtained from step 1) was transferred to a phosgenation tank reactor, and the phosgenation tank reactor had a phosgene inlet pipe, gas-phase condensation reflux and agitation; the phosgenation tank reactor was heated and the agitation was simultaneously operated, and when the temperature reached 60° C., phosgene was introduced, in which a phosgene feeding speed was 50 mol/min, and a reaction temperature was 145° C.; when the reaction liquid was clarified, the feeding was stopped, and a salt-forming phosgenation reaction liquid (crude product) containing the product IPDI, phosgene and o-dichlorobenzene was obtained;

the salt-forming reaction was performed for 0.5 h, the phosgenation reaction was performed for 6 h, and the salt-forming reaction and the phosgenation reaction had a total retention time of 6.5 h;

the reaction tail gas was fed in a tail gas absorption tower and then absorbed with an o-dichlorobenzene solution at −30° C. to obtain an o-dichlorobenzene solution containing phosgene.

b) The reaction liquid obtained from step a) was subjected to a treatment of removing phosgene and the o-dichlorobenzene solution, and the o-dichlorobenzene solution and excess phosgene in the reaction liquid were removed at 145° C. and 0.04 MPa (absolute pressure) to obtain an IPDI crude product without phosgene and an o-dichlorobenzene solution containing phosgene.

c) The o-dichlorobenzene solution containing phosgene obtained from the reaction tail gas absorption in step a) and the o-dichlorobenzene solution containing phosgene obtained from the removal process in step b) were fed in a distillation column for a separation of phosgene and o-dichlorobenzene; the separation process was performed at 0.125 MPa (absolute pressure), a column-bottom temperature of 165° C. and a column-top temperature of 15° C. to obtain phosgene with 98% purity and an o-dichlorobenzene solution with a phosgene content of less than 0.001%, and the separated phosgene and the o-dichlorobenzene solution were all subjected back to step a) for recycling.

d) The IPDI crude product without phosgene obtained from step b) was purified by distillation at 0.5 KPa (absolute pressure) and a distillation range of 140-150° C. to obtain an IPDI (isophorone diisocyanate) product.

An olefin structure, a secondary amine structure and a hydroxyl structure in the IPDA used had a total content of 170 ppm.

The yield of the IPDI product obtained is 97.6% and the product purity is 99.85%. The product obtained contains 35 ppm of hydrolyzed chlorine and 41 ppm of alkaline-dissociated chlorine, and a difference between the alkaline-dissociated chlorine and the hydrolyzed chlorine is 6 ppm.

This example also provides a polyurethane resin, and its preparation method is as follows.

(1) Preparation of Polyurethane Prepolymer

The 100 parts of polyoxypropylene glycol were weighed out, which had a relative molecular mass of 1000, a hydroxyl value of 110 mg KOH/g, a functionality of 2 (Shanghai Gaoqiao Petrochemical Company, polyether polyol GE-210), heated to 110° C. with stirring, subjected to pressure reduction to 200 Pa (absolute pressure) to remove water for 2.5 hours, and cooled to 60° C., and 222 parts of the $H_{12}$MDI produced during the above synthesis of the isocyanate were added. The system was heated to 85° C. and reacted for 150 min to obtain a blue transparent polyurethane prepolymer emulsion.

The turbidity test result for the prepolymer emulsion is 0.32 NTU.

(2) The polyurethane prepolymer obtained from step (1) was prepared into the polyurethane resin and tested for color difference ΔE according to Example 1, and the result is 0.22. It is shown by the data that the polyurethane resin provided by this example has good yellowing resistance.

The obtained polyurethane product was tested for light transmittance according to the method provided by GB/T 2410-2008, and the result is 96.7%.

Example 4

This example provides a polyisocyanate composition, and its preparation method is as follows.

a) diamine IPDA was gasified and heated to 355° C. using the heater disclosed in Example 1 of application CN105214568A, and under the protection of nitrogen, and IPDA and gaseous phosgene that was heated to 355° C. were continuously added to a reactor via their respective feed pipes for a phosgenation reaction; the reaction was performed at 0.05 MPa (absolute pressure) and at 360° C.; IPDA was fed at 800 Kg/h and gaseous phosgene was fed at 3000 Kg/h; the gas mixture obtained from the reaction was cooled rapidly (with a contact time of about 10 s) to 105° C. using a dichlorobenzene solution via a gas injection absorption device to obtain a crude product containing IPDI, phosgene and the dichlorobenzene solution;

the reaction tail gas was fed in a tail gas absorption tower and then absorbed with a dichlorobenzene solution at −25° C. to obtain a dichlorobenzene solution containing phosgene.

b) The crude product obtained from step a) was subjected to a treatment of removing phosgene and dichlorobenzene solvent, and the dichlorobenzene and excess phosgene in the crude product were removed at 168° C. and 0.1 MPa (absolute pressure) to obtain an IPDI crude product without phosgene and a dichlorobenzene solution containing phosgene.

c) The dichlorobenzene solution containing phosgene obtained from the reaction tail gas absorption in step a) and the dichlorobenzene solution containing phosgene obtained from the removal process in step b) were fed in a distillation column for a separation of phosgene and the dichlorobenzene solution; the separation process was performed at 0.125 MPa (absolute pressure), a column-bottom temperature of 155° C. and a column-top temperature of 15° C. to obtain phosgene with 98% purity and a dichlorobenzene solution with a phosgene content of less than 0.001%, and the separated phosgene and the dichlorobenzene solution were all subjected back to step a) for recycling.

d) The IPDI crude product without phosgene obtained from step b) was purified by distillation to obtain an IPDI (isophorone diisocyanate) product at 0.5 KPa (absolute pressure) and a distillation range of 140-150° C.

An olefin structure, a secondary amine structure and a hydroxyl structure in the IPDA used had a total content of 170 ppm.

The yield of the IPDI product obtained is 97.5% and the product purity is 99.85%. The product obtained contains 17 ppm of hydrolyzed chlorine and 22 ppm of alkaline-dissociated chlorine, and a difference between the alkaline-dissociated chlorine and the hydrolyzed chlorine is 5 ppm.

This example also provides a polyurethane resin, and its preparation method is as follows.

(1) Preparation of Polyurethane Prepolymer 100 parts of polyoxypropylene glycol were weighed out, which had a relative molecular mass of 1000, a hydroxyl value of 110 mg KOH/g, a functionality of 2 (Shanghai Gaoqiao Petrochemical Company, polyether polyol GE-210), heated to 110° C. with stirring, subjected to pressure reduction to 200 Pa (absolute pressure) to remove water for 2.5 hours, and cooled to 60° C., and 222 parts of the IPDI produced during the above synthesis of the isocyanate were added. The system was heated to 85° C. and reacted for 150 min to obtain a blue transparent polyurethane prepolymer emulsion.

The turbidity test result for the prepolymer emulsion is 0.19 NTU.

(2) The polyurethane prepolymer obtained from step (1) was prepared into the polyurethane resin and tested for color difference ΔE according to Example 1, and the result is 0.21. It is shown by the data that the polyurethane resin provided by this example has good yellowing resistance.

The obtained polyurethane product was tested for light transmittance according to the method provided by GB/T 2410-2008, and the result is 94.9%.

Example 5

This example provides a polyisocyanate composition, and its preparation method differs from Example 1 only in that an olefin structure, a secondary amine structure and a hydroxyl structure in the HDA used had a total content of 50 ppm; other operation steps and conditions were the same as in Example 1.

The yield of the HDI product obtained is 97% and the product purity is 99.75%. The product obtained contains 25 ppm of hydrolyzed chlorine and 25.4 ppm of alkaline-dissociated chlorine, and a difference between the alkaline-dissociated chlorine and the hydrolyzed chlorine is 0.4 ppm.

This example also provides a polyurethane resin, and its preparation method is the same as in Example 1.

The turbidity of the synthesized emulsion of polyurethane prepolymer is 0.10 NTU; the prepared polyurethane resin was tested for color difference ΔE and the result is 0.09.

The obtained polyurethane product was tested for light transmittance according to the method provided by GB/T 2410-2008, and the result is 98.5%.

Example 6

This example provides a polyisocyanate composition, and its preparation method differs from Example 1 only in that, in step (a), the gas mixture obtained from the reaction was cooled rapidly (with a contact time of about 10 s) to 120° C. using an o-dichlorobenzene solution via a gas injection absorption device; other operation steps and conditions were the same as in Example 1.

The yield of the HDI product obtained is 97% and the product purity is 99.8%. The product obtained contains 23 ppm of hydrolyzed chlorine and 63 ppm of alkaline-dissociated chlorine, and a difference between the alkaline-dissociated chlorine and the hydrolyzed chlorine is 40 ppm.

This example also provides a polyurethane resin, and its preparation method is the same as in Example 1.

The turbidity of the synthesized emulsion of polyurethane prepolymer is 0.11 NTU; the prepared polyurethane resin was tested for color difference ΔE and the result is 0.10.

The obtained polyurethane product was tested for light transmittance according to the method provided by GB/T 2410-2008, and the result is 98.4%.

Example 7

This example provides a polyisocyanate composition, and its preparation method differs from Example 2 only in that an olefin structure, a secondary amine structure and a hydroxyl structure in the $H_{12}MDA$ used had a total content of 120 ppm; other operation steps and conditions were the same as in Example 2.

The yield of the HDI product obtained is 96.2% and the product purity is 99.8%. The product obtained contains 4.1 ppm of hydrolyzed chlorine and 4.3 ppm of alkaline-dissociated chlorine, and a difference between the alkaline-dissociated chlorine and the hydrolyzed chlorine is 0.2 ppm.

This example also provides a polyurethane resin, and its preparation method is the same as in Example 2.

The turbidity of the synthesized emulsion of polyurethane prepolymer is 0.14 NTU; the prepared polyurethane resin was tested for color difference ΔE and the result is 0.15.

The obtained polyurethane product was tested for light transmittance according to the method provided by GB/T 2410-2008, and the result is 96.2%.

Example 8

This example provides a polyisocyanate composition, and its preparation method differs from Example 2 only in that the cold and hot phosgenation reaction stages had a total retention time of six hours, wherein the cold reaction was 5 min, and the hot reaction was 5 hours and 55 minutes; other operation steps and conditions were the same as in Example 2.

The yield of the $H_{12}MDI$ product obtained is 96% and the product purity is 99.8%. The product obtained contains 5 ppm of hydrolyzed chlorine and 65 ppm of alkaline-dissociated chlorine, and a difference between the alkaline-dissociated chlorine and the hydrolyzed chlorine is 60 ppm.

This example also provides a polyurethane resin, and its preparation method is the same as in Example 2.

The turbidity of the synthesized emulsion of polyurethane prepolymer is 0.15 NTU; the prepared polyurethane resin was tested for color difference ΔE and the result is 0.15.

The obtained polyurethane product was tested for light transmittance according to the method provided by GB/T 2410-2008, and the result is 96.0%.

Example 9

This example provides a polyisocyanate composition, and its preparation method differs from Example 3 only in that an olefin structure, a secondary amine structure and a hydroxyl structure in the IPDA used had a total content of 180 ppm; other operation steps and conditions were the same as in Example 3.

The yield of the IPDI product obtained is 97.5% and the product purity is 99.85%. The product obtained contains 17 ppm of hydrolyzed chlorine and 22 ppm of alkaline-dissociated chlorine, and a difference between the alkaline-dissociated chlorine and the hydrolyzed chlorine is 5 ppm.

The yield of the IPDA product obtained is 97.6% and the product purity is 99.87%. The product obtained contains 17.4 ppm of hydrolyzed chlorine and 17.5 ppm of alkaline-dissociated chlorine, and a difference between the alkaline-dissociated chlorine and the hydrolyzed chlorine is 0.1 ppm.

This example also provides a polyurethane resin, and its preparation method is the same as in Example 3.

The turbidity of the synthesized emulsion of polyurethane prepolymer is 0.19 NTU; the prepared polyurethane resin was tested for color difference ΔE and the result is 0.18.

The obtained polyurethane product was tested for light transmittance according to the method provided by GB/T 2410-2008, and the result is 94.0%.

Example 10

This example provides a polyisocyanate composition, and its preparation method differs from Example 3 only in that the salt-forming reaction and the phosgenation reaction had a total retention time of 6 h, in which the salt-forming reaction was 0.5 h, and the phosgenation reaction was 5.5 h; other operation steps and conditions were the same as in Example 3.

The yield of the HDI product obtained is 97.5% and the product purity is 99.88%. The product obtained contains 17 ppm of hydrolyzed chlorine and 117 ppm of alkaline-dissociated chlorine, and a difference between the alkaline-dissociated chlorine and the hydrolyzed chlorine is 100 ppm.

This example also provides a polyurethane resin, and its preparation method is the same as in Example 3.

The turbidity of the synthesized emulsion of polyurethane prepolymer is 0.19 NTU; the prepared polyurethane resin was tested for color difference ΔE and the result is 0.20.

The obtained polyurethane product was tested for light transmittance according to the method provided by GB/T 2410-2008, and the result is 94.8%.

Comparative Example 1

This comparative example provides a polyisocyanate composition, and its preparation method differs from Example 1 only in that, in step (a), the gas mixture obtained from the reaction was cooled rapidly (with a contact time of about 10 s) to 175° C. using an o-dichlorobenzene solution via a gas injection absorption device; other operation steps and conditions were the same as in Example 1.

The yield of the HDI product obtained is 97% and the product purity is 99.74%. The product obtained contains 23 ppm of hydrolyzed chlorine and 170 ppm of alkaline-dissociated chlorine, and a difference between the alkaline-dissociated chlorine and the hydrolyzed chlorine is 147 ppm.

This example also provides a polyurethane resin, and its preparation method is the same as in Example 1.

The turbidity of the synthesized emulsion of polyurethane prepolymer is 1.7 NTU; the prepared polyurethane resin was tested for color difference ΔE and the result is 1.5.

The obtained polyurethane product was tested for light transmittance according to the method provided by GB/T 2410-2008, and the result is 81.5%.

Comparative Example 2

This comparative example provides a polyisocyanate composition, and its preparation method differs from Example 2 only in that the cold reaction had a retention time of 30 min, and the hot reaction had a retention time of 8 h, and the cold and hot phosgenation reaction stages had a total retention time of 8.5 h; other operation steps and conditions were the same as in Example 2.

The yield of the $H_{12}MDI$ product obtained is 96.2% and the product purity is 99.81%. The product obtained contains 3 ppm of hydrolyzed chlorine and 170 ppm of alkaline-dissociated chlorine, and a difference between the alkaline-dissociated chlorine and the hydrolyzed chlorine is 167 ppm.

This example also provides a polyurethane resin, and its preparation method is the same as in Example 2.

The turbidity of the synthesized emulsion of polyurethane prepolymer is 1.9 NTU; the prepared polyurethane resin was tested for color difference ΔE and the result is 1.7.

The obtained polyurethane product was tested for light transmittance according to the method provided by GB/T 2410-2008, and the result is 79.1%.

Comparative Example 3

This comparative example provides a polyisocyanate composition, and its preparation method differs from Example 3 only in that, in step a), the salt-forming reaction and the phosgenation reaction had a total retention time of 9.5 h; other operation steps and conditions were the same as in Example 3.

The yield of the IPDI product obtained is 97.4% and the product purity is 99.86%. The product obtained contains 25 ppm of hydrolyzed chlorine and 131 ppm of alkaline-dissociated chlorine, and a difference between the alkaline-dissociated chlorine and the hydrolyzed chlorine is 106 ppm.

This example also provides a polyurethane resin, and its preparation method is the same as in Example 3.

The turbidity of the synthesized emulsion of polyurethane prepolymer is 0.67 NTU; the prepared polyurethane resin was tested for color difference ΔE and the result is 1.9.

The obtained polyurethane product was tested for light transmittance according to the method provided by GB/T 2410-2008, and the result is 85.5%.

Comparative Example 4

This comparative example provides a polyisocyanate composition, and its preparation method differs from Example 4 only in that an olefin structure, a secondary amine structure and a hydroxyl structure in the IPDA used had a total content of 0.2 ppm; other operation steps and conditions were the same as in Example 4.

The yield of the IPDI product obtained is 97.4% and the product purity is 99.85%. The product obtained contains 21 ppm of hydrolyzed chlorine and 21 ppm of alkaline-dissociated chlorine, and a difference between the alkaline-dissociated chlorine and the hydrolyzed chlorine is 0 ppm.

This example also provides a polyurethane resin, and its preparation method is the same as in Example 4.

The turbidity of the synthesized emulsion of polyurethane prepolymer is 0.75 NTU; the prepared polyurethane resin was tested for color difference ΔE and the result is 0.27.

The obtained polyurethane product was tested for light transmittance according to the method provided by GB/T 2410-2008, and the result is 73.2%.

By comparing Example 1 and Comparative Example 1, Example 2 and Comparative Example 2, Example 3 and Comparative Example 3, and Example 4 and Comparative Example 4, it can be seen that the polyisocyanate composition provided by the present application which contains a specific amount (0.1 ppm-100 ppm difference from hydrolyzed chlorine) of alkaline-dissociated chlorine can effectively prevent the polyurethane synthetic emulsion from becoming turbid, thus improving the light transmittance and yellowing resistance of polyurethane products.

By comparing Examples 1 and 5-10, it can be seen that in the case where a mass content of alkaline-dissociated chlorine minus a mass content of hydrolyzed chlorine has a value of 0.2 ppm-60 ppm in the polyisocyanate composition (Examples 1 and 5-8), the turbidity problem of the polyurethane synthetic emulsion can be further relieved, improving the light transmittance and yellowing resistance of the products, and the result is better when the difference is within 4 ppm-40 ppm (Examples 1 and 5-6).

What is claimed is:

1. A polyisocyanate composition, wherein a mass content of alkaline-dissociated chlorine minus a mass content of hydrolyzed chlorine has a value of 0.1 ppm-100 ppm;

the mass content of the alkaline-dissociated chlorine is a mass content obtained by calculation based on halogen dissociated under alkaline condition and/or halogen dissociated at more than or equal to 100° C. with the relative atomic mass of chlorine atom;

wherein a method for determining the alkaline-dissociated chlorine comprises: firstly, an isocyanate in the polyisocyanate is removed through a reaction between ethanol and polyisocyanate, and then an alkali-dissociable halogen is dissociated down under alkaline conditions, and then a content is determined with silver nitrate standard solution by potentiometric titration.

2. The polyisocyanate composition according to claim 1, wherein the mass content of alkaline-dissociated chlorine minus the mass content of hydrolyzed chlorine has a value of 0.2 ppm-60 ppm.

3. The polyisocyanate composition according to claim 1, wherein the polyisocyanate composition comprises a combination of polyisocyanate, and an alkaline-dissociated chlorine impurity.

4. The polyisocyanate composition according to claim 1, wherein a raw material for preparation comprises a combination of polyamine and a phosgene raw material;

impurities having an olefin structure, a secondary amine structure or a hydroxyl structure in the polyamine have a total mass content of 0.1 ppm-400 ppm.

5. A preparation method of the polyisocyanate composition according to claim 1, comprising: subjecting polyamine and a phosgene raw material to a phosgenation reaction to obtain the polyisocyanate composition.

6. The preparation method according to claim 5, wherein the phosgenation reaction comprises a gas-phase phosgenation reaction, a liquid-phase phosgenation reaction or a salt-forming phosgenation reaction.

7. A polyurethane resin, wherein a raw material to prepare the polyurethane resin comprises a combination of the polyisocyanate composition according to claim 1 and a compound containing a reactive hydrogen group.

8. The polyurethane resin according to claim 7, wherein the compound containing a reactive hydrogen group comprises a polyol compound and/or an amine compound.

9. The polyurethane resin according to claim 7, wherein the raw material to prepare the polyurethane resin further comprises a catalyst and/or a chain extender.

10. A method for preparing polyurethane elastomers, polyurethane optical materials, polyurethane coating materials or polyurethane foams by using the polyurethane resin according to claim 7.

11. The polyisocyanate composition according to claim 3, wherein the polyisocyanate is diisocyanate.

12. The polyisocyanate composition according to claim 3, wherein the polyisocyanate comprises any one or a combination of at least two of alicyclic diisocyanate, aromatic diisocyanate or chain diisocyanate.

13. The polyisocyanate composition according to claim 3, wherein the polyisocyanate comprises any one or a combination of at least two of dicyclohexylmethane diisocyanate, isophorone diisocyanate, hexamethylene diisocyanate, m-xylylene diisocyanate, p-xylylene diisocyanate, 1,3-dimethyl isocyanate cyclohexane, 1,4-dimethyl isocyanate cyclohexane, tetramethylene diisocyanate, pentamethylene diisocyanate, toluene diisocyanate, diphenylmethane diisocyanate, benzene diisocyanate, naphthalene diisocyanate or cyclohexyl diisocyanate.

14. The preparation method according to claim 6, wherein the gas-phase phosgenation reaction comprises: subjecting a polyamine gas stream and the phosgene raw material to a gas-phase phosgenation reaction, and mixing a reaction product with a liquid inert medium and cooling to less than or equal to 150° C., or, mixing a reaction product with a liquid inert medium and a target isocyanate product mixture and cooling to less than or equal to 150° C.

15. The preparation method according to claim 6, wherein the liquid-phase phosgenation reaction comprises: subjecting a polyamine solution and the phosgene raw material to a cold reaction at 0-100° C. and then to a hot reaction at 60-180° C., wherein the cold reaction and the hot reaction have a total retention time of less than or equal to 7 h.

16. The preparation method according to claim 6, wherein the salt-forming phosgenation reaction comprises: subjecting the polyamine, hydrogen chloride and/or carbon dioxide to a salt-forming reaction in an inert solvent, and then subjecting the system and the phosgene raw material to a phosgenation reaction; the salt-forming reaction and the phosgenation reaction have a total retention time of less than or equal to 7 h.

17. The preparation method according to claim 8, wherein the polyol compound has a molecular mass of 400-20000;

the polyol compound has a hydroxyl value of 10 mg KOH/g-1500 mg KOH/g;

the polyol compound has a functionality of 2-8.

* * * * *